United States Patent
Lanzi et al.

(10) Patent No.: US 10,953,161 B2
(45) Date of Patent: Mar. 23, 2021

(54) DEVICE AND METHOD FOR SAFE AND EASY REMOVAL OF A NEEDLE SHIELD ELEMENT FROM A PHARMACEUTICAL SYRINGE

(71) Applicant: Hoffmann-La Roche Inc., Little Falls, NJ (US)

(72) Inventors: Sylvain Lanzi, Basel (CH); Maxime Gaillot, Basel (CH); Rasmus Oehlenschlaeger, Gentofte (DK)

(73) Assignee: Hoffmann-La Roche Inc., Little Falls, NJ (US)

( * ) Notice: Subject to any disclaimer, the term of this patent is extended or adjusted under 35 U.S.C. 154(b) by 281 days.

(21) Appl. No.: 16/058,105

(22) Filed: Aug. 8, 2018

(65) Prior Publication Data
US 2018/0344948 A1    Dec. 6, 2018

Related U.S. Application Data

(63) Continuation of application No. PCT/EP2017/052585, filed on Feb. 7, 2017.

(30) Foreign Application Priority Data

Feb. 8, 2016    (EP) .................................... 16154644

(51) Int. Cl.
*A61M 5/32*    (2006.01)

(52) U.S. Cl.
CPC ........ *A61M 5/3204* (2013.01); *A61M 5/3202* (2013.01); *A61M 2005/3215* (2013.01)

(58) Field of Classification Search
CPC .... A61M 5/50; A61M 25/0618; A61M 5/321; A61M 5/3213; A61M 5/3202; A61M 2005/3215; A61M 5/3204; A61B 50/3001
See application file for complete search history.

(56) References Cited

U.S. PATENT DOCUMENTS

2015/0165129 A1*  6/2015  Row .................... A61M 5/482
                                                                 604/189

FOREIGN PATENT DOCUMENTS

WO            89/02758 A1    4/1989
WO    WO-2015044561 A1 *  2/2015
(Continued)

OTHER PUBLICATIONS

Patrick Perche, English translation of WO2015044561 (Year: 2015).*
(Continued)

*Primary Examiner* — Theodore J Stigell
*Assistant Examiner* — Daniel Moore
(74) *Attorney, Agent, or Firm* — Medler Ferro Woodhouse & Mills PLLC

(57) ABSTRACT

A device for safe and easy removal of a rigid needle shield from a syringe, said device comprising a wall with an inner and an outer surface, the inner surface of the wall defining a tubular hollow portion along the longitudinal axis of the a rigid needle shield, said inner wall comprising a recess adapted to receive a compressible gasket movable within said recess along said longitudinal axis from a portion of the recess wherein said gasket is in a relatively uncompressed state to a portion of said recess wherein said gasket is in a relatively compressed state compared to the relatively uncompressed state, wherein said recess is arranged so that the gasket grips the rigid needle shield in the compressed state.

8 Claims, 6 Drawing Sheets

(56) References Cited

FOREIGN PATENT DOCUMENTS

| WO | 2015/044561 A1 | 4/2015 |
| WO | 2015/073740 A2 | 5/2015 |

OTHER PUBLICATIONS

International Search Report dated Apr. 18, 2017 in corresponding International Patent Application No. PCT/EP2017/052585.

* cited by examiner (A)          (B)          (C)

DEVICE AND METHOD FOR SAFE AND EASY REMOVAL OF A NEEDLE SHIELD ELEMENT FROM A PHARMACEUTICAL SYRINGE

RELATED APPLICATIONS

This application is a continuation of international patent application number PCT/EP2017/052585, filed Feb. 7, 2017, which claims benefit of priority to European patent application number EP16154644.5, filed Feb. 8, 2016, each of which is incorporated herein by reference in its entirety.

The present invention relates to a device and method for safe and easy removal of a needle shield element from a pharmaceutical syringe.

Self-injection of pharmaceutical products by users is becoming increasingly common, such as among such as diabetic users for example. Syringes are typically capped with a needle shield to prevent accidental injections. In some instances, the needle shield can be rigid and is a so-called rigid needle shield (RNS). For certain user populations with reduced strength and mobility in their hands, removing a rigid needle shield can be very difficult. This is the case for rheumatoid arthritis users for example. Standard rigid needle shields are small and offer gripping portions that may be unsuitable, for example, for rheumatoid arthritis users. These users may not be able to uncap the syringe at all. Some users have reportedly tried unsafe methods to uncap syringes, such as using their teeth, and accidents have consequently occurred.

There is a need for means to uncap syringes in a safe and easy way for certain users. Recognizing this need, the pharmaceutical industry has offered solutions such as described in published PCT patent application WO2009090499 in which the solution to removing a standard rigid needle shields was to provide a syringe in which the needle shield is fitted with a needle tip cap having a gripping portion for easier removal of the needle shield. The needle tip cap engages with the needle shield by means of protrusions and recesses design that requires a relatively complicated manufacturing process so as to be functional. This complexity leads to relatively high prices and further requires the syringe assembly of the needle tip cap and the needle shield and syringe to be preassembled prior to packaging.

There is still a need for a device for safe and easy removal of a rigid needle shield from a syringe that is easy and cheap to manufacture.

The inventors provide herein a device for a safe an easy removal of a rigid needle shield from a syringe that is relatively cheaper and easier to manufacture than existing devices in the art.

In one embodiment, the invention relates to a device for safe and easy removal of a rigid needle shield from a syringe, said device comprising a wall with an inner and an outer surface, the inner surface of the wall defining a tubular hollow portion along the longitudinal axis of the a rigid needle shield, said inner wall comprising a recess adapted to receive a compressible gasket movable within said recess along said longitudinal axis from a portion of the recess wherein said gasket is in a relatively uncompressed state to a portion of said recess wherein said gasket is in a relatively compressed state compared to the relatively uncompressed state, wherein said recess is arranged so that the gasket grips the rigid needle shield in the compressed state.

In another embodiment, the invention relates to a method for safe and easy removal of a rigid needle shield using a device according to the invention.

Further aspects of the method according to the invention will become apparent from the following detailed description and will be exemplified with the non-limiting embodiments depicted in FIGS. 1 to 6:

Figure 1:
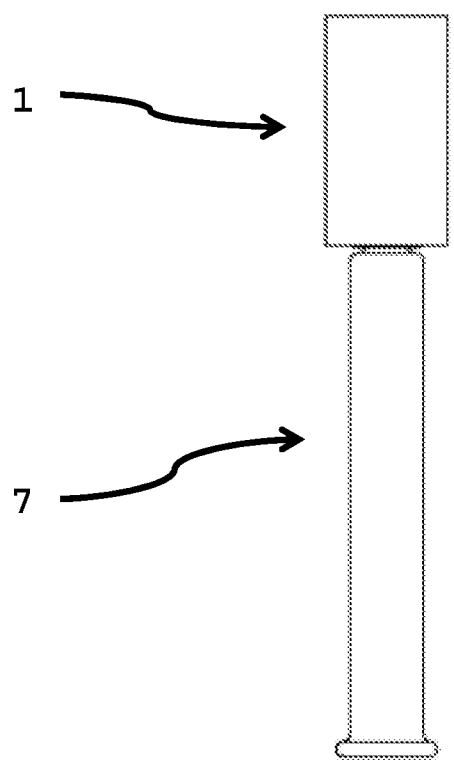
FIG. 1 shows an embodiment of the device according to the invention when in use, positioned on a rigid needle shield.

As shown in the embodiment depicted in FIG. 1, the device according to the invention (1) comprises a wall (2) with an inner (21) and an outer surface (22), the inner surface (21) of the wall defining a tubular hollow portion (3) along the longitudinal axis of the a rigid needle shield (6) of a syringe (7), said inner wall comprising a recess (4) adapted to receive a compressible gasket (5) movable within said recess along said longitudinal axis from a portion of the recess wherein said gasket is in a relatively uncompressed state to a portion of said recess wherein said gasket is in a relatively compressed state, wherein said recess is arranged so that the gasket grips the rigid needle shield (6) in the compressed state.

Because the device according to the invention is of simple design and easy to use, it does not need to be preassembled with the syringe in the package provided to the end user. One of the advantages is that it can be used with any standard rigid needle shield and can simply be added to the drug product packaging. The device according to the invention can of course also be preassembled, if suitable, and delivered as such in a package to the end user.

Figure 3:
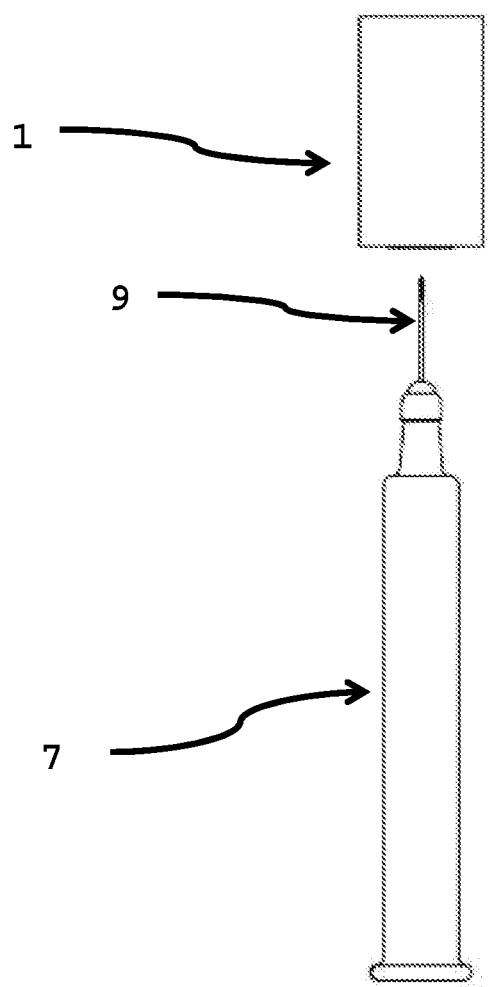
FIG. 3 shows an embodiment of the device according to the invention when in use, after removal of the rigid needle shield from the syringe's needle.

FIGS. 1 and 3 show general view of two consecutive steps the users take when using the device according to the invention. FIG. 1 shows the step where the user has inserted the device according to the invention (1) on the rigid needle shield (the riding needle shield is not shown) that protects the needle on the syringe (7). FIG. 3 shows the step where the user has removed the rigid needle shield from the needle of the syringe by pulling the device according to the invention (1) away from the syringe (7). In this step, the rigid needle shield is removed and captured by the device according to the invention.

Figure 2:
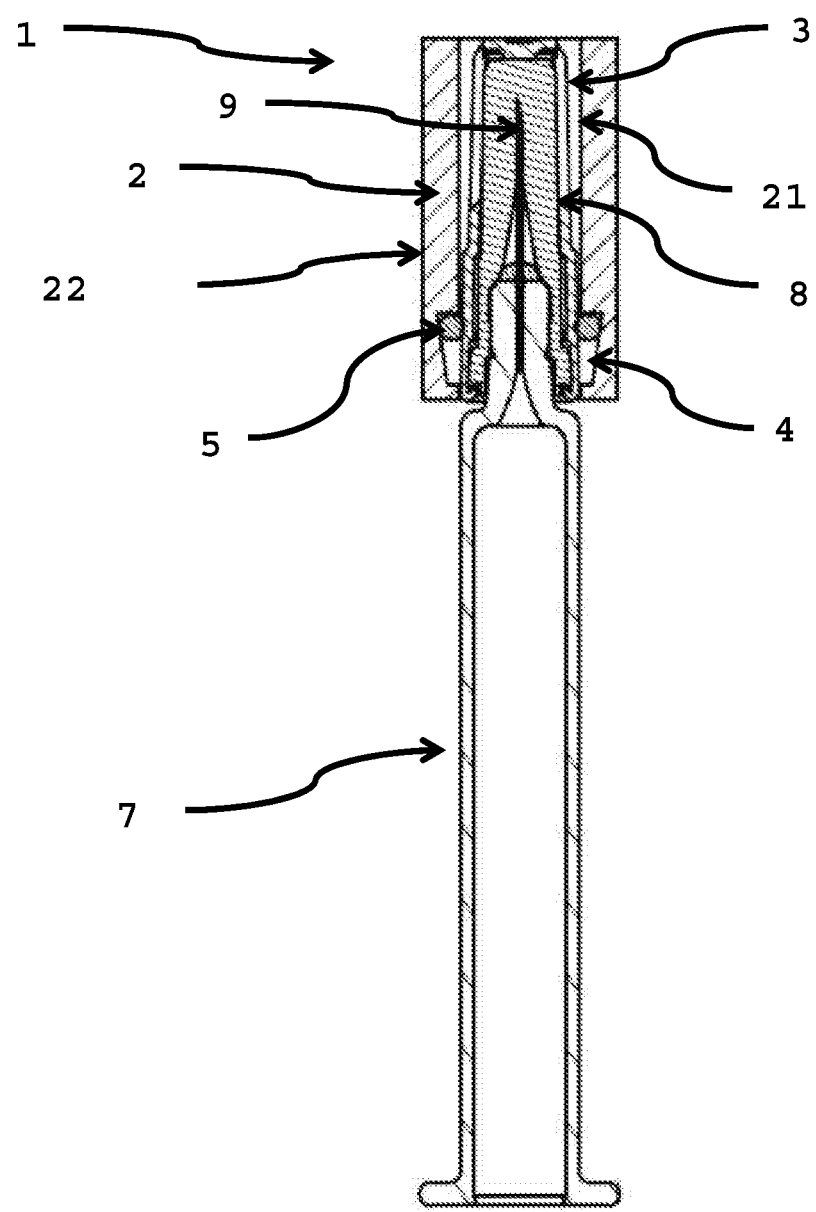
FIG. 2 shows a cross-sectional view of the embodiment of FIG. 1.
Figure 4:
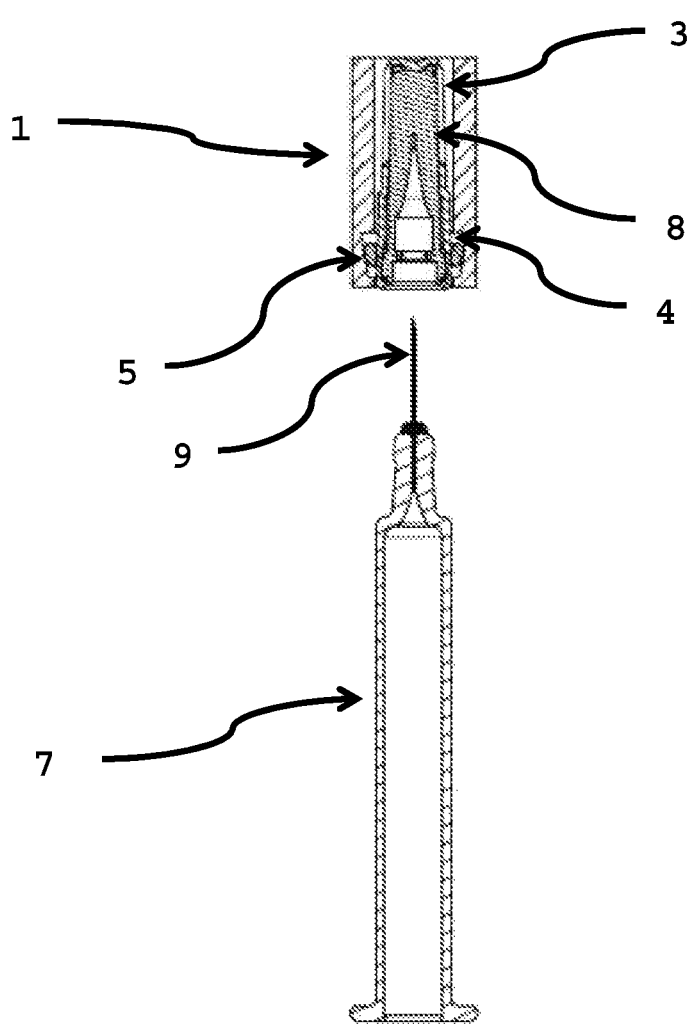
FIG. 4 shows a cross-sectional view of the embodiment of FIG. 3.

FIGS. 2 and 4 show cross-sectional views of the steps described in FIGS. 1 and 3. These figures show how, in an embodiment, the device according to the invention enables removing and capturing the rigid needle shield. In FIG. 2, the rigid needle shield (8) is still in an initial position, protecting the needle (9) of the syringe (7). In this embodiment, the device (1) comprises a wall with an inner surface (21) defining a tubular hollow portion (3) that encompasses the rigid needle shield (8). The inner surface (21) comprises a recess (4), which in this embodiment has the shape of a truncated cone in the inner surface (21) of the wall (2) of the device (1) along the longitudinal axis of the tubular hollow portion (3). The recess having the shape of truncated cone has a base that has a larger surface than its top. The gasket (5) is located in the recess near the base of the truncated cone and is in a relatively uncompressed state. FIG. 4 shows a cross-sectional view of the step where the user has removed the rigid needle shield from the needle of the syringe by pulling the device according to the invention (1) away from the syringe (7). In this step, the rigid needle shield is removed and captured by the device according to the invention. Removal and capture of the rigid needle shield (8) is enabled by the fact that the gasket (5) is moved from the base of truncated cone recess toward its top along the longitudinal axis of the tubular hollow portion (3) by the action of the user pulling the device (1) away from the needle, thereby compressing the gasket and exerting a pressure on the rigid needle shield that is sufficient to remove and capture it.

The device according to the invention can have a great variety of shapes. The shape of the device can suitably be chosen to allow for a good grip by the user. It can for example comprise a gripping portion to enhance gripping by the user. This gripping portion can comprise grooves and/or protrusions in a plane that is more or less perpendicular to the axis of the syringe. More or less perpendicular means in the context of the present invention that the plane(s) in which the grooves and or protrusions are arranged is (are) at an about between 70 to 110 degrees angle relatively to the axis of the syringe, or for example 90 degrees. The gripping portion can also be made of another material than of the device of the invention and can be permanently attached to the device of the invention by any suitable means such as clipped, glued or welded onto the device. The device can also comprise a gripping loop or any kind of shape that allows for an easy handling by the user.

The recess (4) can also have a variety of shapes as long as it performs the require function of compressing the gasket by reduction of the space between the interior wall surface of the hollow tubular portion (3) and the surface of the rigid needle shield (8) when the gasket is moved along the longitudinal axis of the tubular portion (3) by action of the user pulling the device (1).

Figure 6:
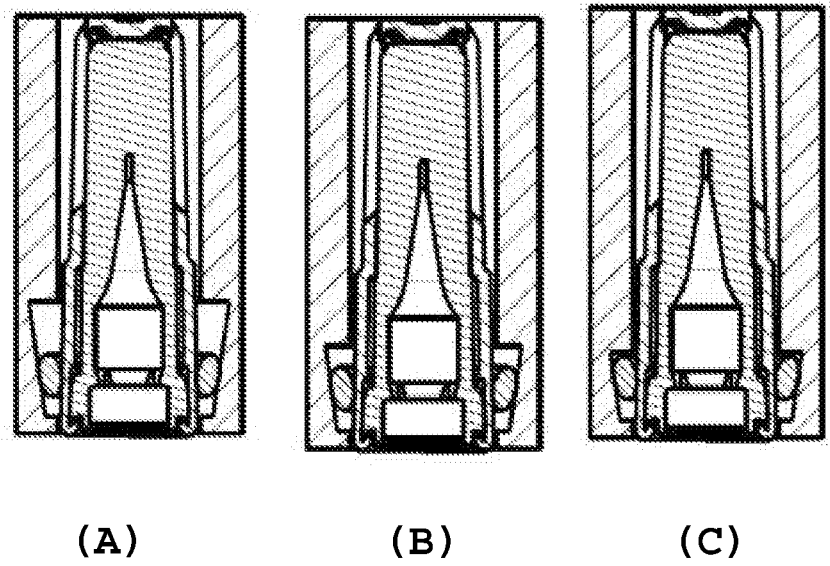
FIG. 6 shows a cross-sectional view of various embodiments of the device according to the invention.

FIG. 6 shows different embodiments of the device according to the invention, wherein the recess is conical and has various sizes and shapes. In these embodiments, the length of the conical recess along the longitudinal axis of the tubular portion can vary, thereby allowing for different compression states, as a function of the movement of the gasket along this axis and the shape of the recess.

Figure 5:
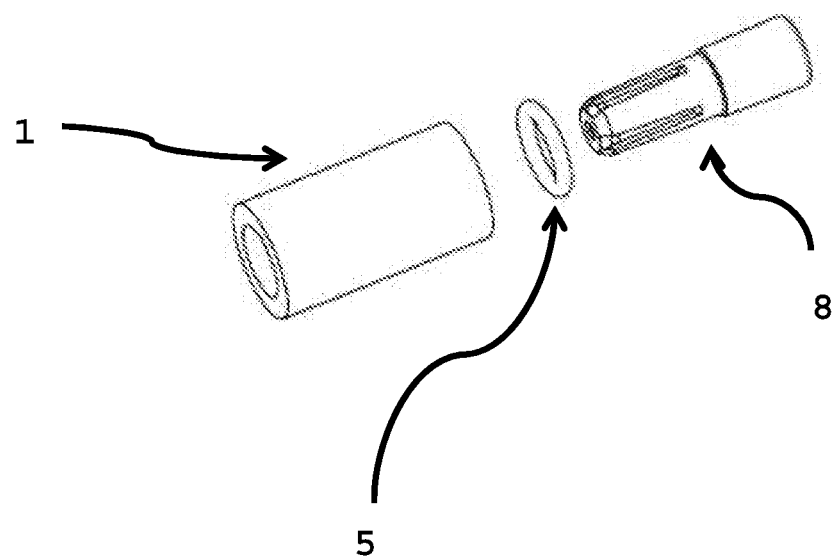
FIG. 5 shows an exploded view of the device according to the invention together with a rigid needle shield.

FIG. 5 shows an exploded view of an embodiment of the device according to the invention (1). In this embodiment, the device of the invention comprises only two elements, the device (1) and a gasket (5). This embodiment is very easy to manufacture and much cheaper compared to existing devices therefore facilitating access to users who need it.

The device according to the invention can be made of any suitable material. The material can be chosen among pharmaceutically acceptable material such as pharmaceutical plastic packaging material, for example, polyethylene (PE), polypropylene (PP), polycarbonate (PC) acrylonitrile butadiene styrene (ABS) or polyoxymethylene (POM). The material of the device of the invention can also be suitably chosen among so-called GRAS material such as published by the FDA. GRAS are substances considered "Generally Recognized As Safe (GRAS)" in food packaging. These materials could be used as well as long as they satisfy the purpose and function of the device of the invention: http://www.fda.gov/Food/IngredientsPackagingLabeling/GRAS/

The gasket (5) can be made of any suitable compressible material, for example from elastomer known in the art. An example of such material can be a thermoplastic elastomer (TPE), a natural or a synthetic rubber. The gasket can suitably be an O-ring gasket. An O-ring gasket typically has a circular or oval section, but any other shape can be used such as a ring gasket having a square or triangle section. Standard gaskets such as already available commercially can be used. This means that this element does not need to be custom made and also allows for cheaper and easier manufacturing processes compared to existing devices in the art.

Within the context of this patent application, the expression "from a relatively uncompressed state to a relatively compressed state" means that the gasket is less compressed in an uncompressed state than in the compressed state. This also means that the gasket can be uncompressed or slightly compressed in the uncompressed state, but relatively less compressed than in the compressed state. Relative state of compression can be measured by methods known in the art. For instance, this relative compression can, for example, be measured by standard compression force measures wherein the material compression expressed in percentage is measured as a function of the pressure applied for example in psi. Relative state of compression can also be deducted from a calculation of the volume available in the recess for the gasket at relative positions when it is moved within the recess along the longitudinal axis of the tubular hollow portion (3). Therefore, in one embodiment, the invention relates to a device for safe and easy removal of a rigid needle shield from a syringe, said device comprising a wall with an inner and an outer surface, the inner surface of the wall defining a tubular hollow portion along the longitudinal axis of the a rigid needle shield, said inner wall comprising a recess adapted to receive a compressible gasket movable within said recess from a relatively uncompressed state to a relatively more compressed state compared to the relatively uncompressed state, wherein said recess is arranged so that the gasket grips the rigid needle shield in the compressed state.

Within the context of the invention "grips" or "gripping" means that the gasket is sufficiently compressed so as to exert a compression force that is high enough to "grip", i.e. allow removal of the rigid needle shield when the user pulls on the device according to the invention.

In one embodiment of the device according to the invention the retention force ranges from about 60 to about 100 Newtons, or for example from about 60 to 80 Newtons.

In one embodiment, the device according to the invention is a device for safe and easy removal of a rigid needle shield from a syringe, said device comprising a wall with an inner and an outer surface, the inner surface of the wall defining a tubular hollow portion along the longitudinal axis of the a rigid needle shield, said inner wall comprising a recess adapted to receive a compressible gasket movable within said recess from a slightly compressed state to a more compressed state, wherein said recess is arranged so that the gasket grips the rigid needle shield in the compressed state.

In one embodiment, the device according to the invention is a device for safe and easy removal of a rigid needle shield from a syringe, said device comprising a wall with an inner and an outer surface, the inner surface of the wall defining a tubular hollow portion along the longitudinal axis of the a rigid needle shield, said inner wall comprising a recess adapted to receive a compressible gasket movable within said recess from an uncompressed state to a compressed state, wherein said recess is arranged so that the gasket does not grip the rigid needle shield in the uncompressed state and grips the rigid needle shield in the compressed state. In one embodiment, the compression of the gasket is due to the displacement of the gasket in the recess when the user is pulling on the rigid needle shield. The gasket is forced into a portion of the cone shape of the recess that offers less volume for the gasket and the gasket is thereby compressed. For example, compression of the gasket can be achieved by a reduction of the available volume for the gasket by 5 to 80% at the end position of the gasket when moving along the longitudinal axis of the tubular portion in the recess as compared to the initial position of the gasket in said recess. Examples of reduction of said available volume can also range from 10 to 70% or 15 to 65% or 20 to 50% or 20 to 40% or 25 to 35%. The available volume can be calculated based on an approximation of the shape of the gasket. For example, if the gasket is an O-ring, the approximate available volume can be calculated as a tor at a particular location within the recess. The compression also depends on the removal force (expressed in Newtons) applied to the rigid needle shield until it reaches a value that enables removal of the rigid needle shield from the needle.

FIG. 6 shows three different designs of devices according to the invention that were tested, with variations of the dimensions of the truncated cone. All the designs allow removing the needle shield from the syringe as the retention force (force required to remove the device from the rigid needle shield) is higher than the needle shield removal force. The table below presents differences of measured retention forces:

| Design reference | Retention force (in N) |
|---|---|
| Design A | 67.9 |
| Design B | 62.4 |
| Design C | 80.3 |

Despite its apparent manufacturing simplicity, the device according to the invention is surprisingly efficient for removing and capturing rigid needle shields. The inventors were surprised by the data collected upon testing the device according to the invention and comparing with other devices. Common sense would indeed dictate that devices with mechanical gripping means, such as described in WO2009090499 would provide for a much stronger retention force compared to a gasket such as in the device according to the invention. The inventors discovered that using a gasket and gripping a rigid needle shield by friction could be as efficient as by gripping, therefore offering a much simpler, cheaper alternative to mechanical gripping means known in the art. Using a gasket can be seen as an indirect mean of connection between parts as the mechanical connection is performed by the movement of the user thanks to the friction when removing the needle shield.

While the invention has been explained with the aid of embodiments, the invention is not limited to these embodiments. Rather, variations and alternatives are conceivable without departing from the teaching of the invention. Therefore, the scope of protection is defined by the appended claims.

The invention claimed is:

1. A device for safe and easy removal of a rigid needle shield from a syringe,
said device comprising a compressible gasket and a wall with an inner surface and an outer surface, the inner surface of the wall defining a tubular hollow portion along a longitudinal axis of the device
wherein said inner surface of the wall comprises a recess adapted to receive the compressible gasket movable within said recess along said longitudinal axis from a first portion of the recess, wherein said gasket is in a relatively uncompressed state, to a second portion of said recess, wherein said gasket is in a relatively compressed state compared to the relatively uncompressed state,
wherein said recess is arranged so that the gasket grips the rigid needle shield in the relatively compressed state,
and wherein said recess is shaped to compress said gasket by reduction of a space defined between the inner surface of the wall that defines the tubular hollow portion and a surface of the rigid needle shield when said gasket is moved along the longitudinal axis of the device between the first portion and the second portion of said recess by action of a user pulling the device relative to the rigid needle shield.

2. The device of claim 1, wherein the recess is a truncated conical recess having a circular base and wherein the gasket is in the relatively compressed state when moved away from the circular base from the first portion to the second portion.

3. The device of claim 1, wherein the gasket is a circular gasket.

4. The device of claim 3, wherein the circular gasket is an O-ring.

5. The device of claim 1, wherein the gasket comprises a material selected from thermoplastic elastomer (TPE) or natural or synthetic rubber.

6. The device of claim 1, wherein the device comprises a material selected from the group consisting of polyethylene (PE), polypropylene (PP), polycarbonate (PC), acrylonitrile butadiene styrene (ABS) or polyoxymethylene (POM).

7. A method for safe and easy removal of a rigid needle shield from a syringe comprising:
inserting a device onto the rigid needle shield, the device comprising
a wall with an inner surface and an outer surface, the inner surface of the wall defining a tubular hollow portion along a longitudinal axis of the device, wherein the inner surface includes a recess adapted to receive a compressible gasket movable within the recess along the longitudinal axis from a first portion of the recess in which the gasket is in a relatively uncompressed state to a second portion of the recess in which the gasket is in a relatively compressed state;
compressing the gasket from the relatively uncompressed state to the relatively compressed state by pulling the device away from the syringe so as to cause the gasket to move from the first portion of the recess to the second portion of the recess and thereby cause compression of the gasket; and
removing the rigid needle shield from the syringe by pulling the device away from the syringe.

8. The method of claim 7, wherein said recess is shaped to compress said gasket by reduction of a space defined between the inner surface of the wall that defines the tubular hollow portion and a surface of the rigid needle shield as the recess extends from the first portion to the second portion thereof along the longitudinal axis of the device.

* * * * *